United States Patent [19]

Federle et al.

[11] Patent Number: 4,615,342
[45] Date of Patent: Oct. 7, 1986

[54] DEVICE FOR DETERMINING CONTINUOUSLY THE HARDNESS OF A SMOKABLE ARTICLE

[75] Inventors: Hartmut Federle, Ahrensburg; Friedrich Walther, Bargteheide, both of Fed. Rep. of Germany

[73] Assignee: B.A.T. Cigaretten-Fabriken GmbH, Hamburg, Fed. Rep. of Germany

[21] Appl. No.: 699,629

[22] Filed: Feb. 8, 1985

[30] Foreign Application Priority Data

Feb. 9, 1984 [DE] Fed. Rep. of Germany ....... 3404635

[51] Int. Cl.$^4$ ................................................ A24C 5/14
[52] U.S. Cl. .................................... 131/84.1; 131/280; 131/906
[58] Field of Search .............. 131/31, 84 R, 84 B, 131/84 C, 84 A, 280, 906; 73/78; 374/142, 143, 179

[56] References Cited

U.S. PATENT DOCUMENTS

| 2,667,172 | 1/1954 | Broekhuysen et al. | 131/84.1 |
| 3,954,112 | 5/1976 | Brackmann et al. | 131/84.3 |
| 4,028,943 | 6/1977 | Hyanova et al. | 374/143 |
| 4,033,360 | 7/1977 | Nienow et al. | 131/84.3 |
| 4,262,532 | 4/1981 | Butler et al. | 374/143 |
| 4,306,573 | 12/1981 | Rudszinat | 131/84.4 |
| 4,423,742 | 1/1984 | Reuland | 131/84.4 |
| 4,485,826 | 12/1984 | Holzangel | 131/84.4 |
| 4,488,562 | 12/1984 | Remington | 131/31 |
| 4,535,789 | 8/1985 | Irving et al. | 131/84.2 |

*Primary Examiner*—V. Millin
*Assistant Examiner*—H. Macey
*Attorney, Agent, or Firm*—Armstrong, Nikaido, Marmelstein & Kubovcik

[57] ABSTRACT

A device for determining continuously the hardness of a smokable artiele, more particularly a cigarette, from the mechanical properties of a rod of tobacco fibres during the manufacture of this smokable article, which ascertains the temperature of the former finger which compacts the rod of tobacco fibres to a predetermined diameter dependent on the diameter of the finished smokable article. This temperature measurement, which can be carried out by a thermocouple element, a resistance thermometer or a semiconductor temperature sensor, represents an exact reproducible measure of the hardness of the smokable article which is produced with this rod of tobacco fibres.

10 Claims, 5 Drawing Figures

DEVICE FOR DETERMINING CONTINUOUSLY THE HARDNESS OF A SMOKABLE ARTICLE

BACKGROUND OF THE INVENTION (1) Field of the Invention

The invention relates to a device for the continuous determining of the hardness of a smokable article from the mechanical properties of a rod of tobacco fibres in the manufacture of such a smokable article with a former finger for compacting the rod of tobacco fibres to a given diameter.

2. Description of the Prior Art

In cigarette production, more and more attention is being devoted to the hardness of the cigarettes at the quality control stage, since it is possible to determine in a relatively simple manner from measuring the hardness whether a smokable article, for example a cigarette, is adequately filled or not. And it is precisely the inadequate filling of smokable articles which is a frequent ground for complaints.

Therefore, in an article from "Contributions to tobacco research", Vol. 4, Number 7, December, 1968, a device for testing the hardness of cigarettes is described with which the changes in diameter of cigarettes under specific loads is measured over a given time and the hardness is ascertained therefrom. But this substantially static process is suitable only for selected sample tests, in other words cannot be used for current continuous monitoring of the hardness of the smokable articles during manufacture and for appropriate regulation of the whole production operation.

U.S. Pat. No. 3,411,513 also shows a method wherein a moved, finished, tobacco rod wrapped in paper is deformed by a stream of air, and the associated follow-up of the nozzle is ascertained. The nozzle movement which occurs has a correlation with the filling ability of the tobacco and thus the hardness of the cigarette. But the information obtained in this way is influenced by diameter fluctuations and the porosity of the cigarette paper, so that only in a few cases is there a precise correlation with the static measurement of hardness via the determining of depth of penetration as is known from the cited article.

Methods are also known wherein the deformation of the format or former finger under the influence of the stream of tobacco fibres flowing past is ascertained and a continuous measurement signal is thus obtained which is to be correlated to the hardness of the finished cigarette. For example German OS No. 2 241 774 shows a device wherein a force pickup, generally a strain gauge, is provided which ascertains the deformation of the supporting bridge for the former finger. Another variant is known from German OS No. 2 457 141, wherein the deflection of the front portion of the divided former finger under the action of the rod of tobacco fibres is ascertained. And finally U.S. Pat. No. 2,667,172 shows a device which at various places ascertains the vertical and horizontal forces which the rod of tobacco exerts on its guide and more particularly on the former finger. For example the width of the gap between the front end of the former finger and a pickup i.e. the deflection of the front end of the former finger, is ascertained.

In the case of all these known measuring methods, however, the correlation between the deformation of the former finger and the hardness of the finished cigarette is relatively slight i.e. the measurement result correlates linearly with the hardness of the finished cigarette only in situations where the pickup ascertains the deformation of the former finger at a place where the diameter of the skein of tobacco fibres corresponds approximately to the tobacco diameter of the finished smokable article, as is known from the older application No. P 33 06 543.8-23.

SUMMARY OF THE INVENTION

Therefore, the invention has as its object to provide a device for the continuous determining of the hardness of a smokable article from the mechanical properties of a rod of tobacco fibres during the manufacture of this smokable article which, in a simple manner as regards measurement technique, delivers a very precise measure of the hardness of the finished smokable article, namely a measurement signal which is in a linear correlation with the hardness of the finished smokable article.

This object is achieved according to the invention by a pickup ascertaining the temperature of the former finger.

Advantageous forms of embodiment are listed in the subordinate claims.

The advantages obtained with the invention are based on the fact that the heat produced by frictional forces between the rod of tobacco fibres and the underside of the former finger, and thus the corresponding temperature of the former finger, is correlated very precisely with the hardness of the finished smokable article, i.e. a monitoring of the former finger temperature which is simple to carry out as regards measuring technique delivers a very precise measure of the hardness of the smokable article produced. Thus it is possible to conclude from a deviation of the former finger temperature from a predetermined desired value that there will be a corresponding deviation of the hardness of the finished smokable article, so that regulation of the various production parameters in order to cancel this deviation is possible.

The optimum correlation between temperature measurement and smokable article hardness is obtained if the temperature pickup situated in a bore of the former finger bears on the surface of the rod of tobacco fibres. But this gives rise to production process problems, since the tobacco fibres may catch in the mouth of this bore. The measuring element proper is also subjected to relatively rapid wear.

But for practical requirements it is sufficient if the measurement pickup is arranged in a blind hole of the former finger and if the end wall thickness of this blind hole is as slight as possible, for example in the region of 0.1 mm. As a result the temperature pickup is protected from direct contact with the rod of tobacco fibres, without causing any relevant impairment of the correlation between the temperature measurement and the hardness of the finished smokable article.

According to a preferred form of embodiment the temperature of the former finger is ascertained at a place where the diameter of the rod of tobacco fibers corresponds approximately to the tobacco diameter of the finished smokable article, since at this place the compaction of the rod of tobacco fibres is exactly equal to the compaction of the tobacco in the finished smokable article, in other words in this respect condictions are equivalent to those of the finished smokable article; moreover the frictional forces and thus the temperature of the former finger reflect this equivalence with the finished smokable article, so that particularly good correlation is obtained.

It is possible to provide in addition to the actual temperature pickup a compensation temperature pickup for example at the entry end of the former finger, using the difference between the measurement values of the two temperature pickups as a measure of the hardness of the finished smokable article. In this way an automatic compensation of environment influences is obtained, namely ambient temperature and any air flows which otherwise could falsify the measurement result.

These difference measurements also provide information on the compressibility of the cigarette.

For calibration of this device it is simply necessary to ascertain the absolute value of the former finger temperature in the usual operating conditions relevant here, namely especially the speed at which the rod of tobacco fibres is transported, which lead to achieving an optimum hardness for the finished smokable article. Then any deviation from this reference value can be counteracted by adjustment of the appropriate production parameters.

This dependence of the measurement result on steady-state production operation means that under unstable conditions, for example when starting-up a cigarette machine, no utilisable information results.

More particularly resistance thermometers, thermocouple elements and semiconductor temperature sensors are suitable as temperature pickups, that is to say temperature pickups with small and precisely defined measuring heads which can be inserted without any problem in suitable bores in the former finger.

BRIEF DESCRIPTION OF THE DRAWINGS

The invention will be described in more detail hereinafter with the use of examples of embodiments with reference to the accompanying diagrammatic drawings. In these drawings

DESCRIPTION OF THE PREFERRED EMBODIMENTS

Figure 1:
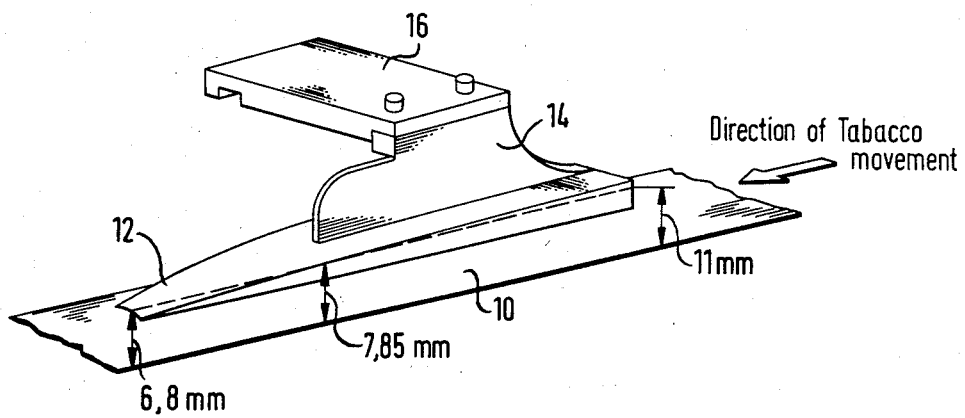
FIG. 1 shows a perspective view of the former finger and the former band of a cigarette machine.

FIG. 1 shows part of a conventional cigarette machine in which the substantially cylindrical rod of tobacco fibres carried-in in the direction of the arrow, is compressed from a diameter of approximately 11 mm to the desired diameter of approximately 6.8 mm; in the course of this, the tobacco rod lying on the former band 10 is compressed to the desired diameter by the format or former finger 12 which is approximately in the shape of a hollow half-cylinder.

As FIG. 1 shows, the former finger 12 is secured to a vertically situated, relatively rigid plate 14 which in its turn is arranged on a horizontal support 16.

Assuming that the tobacco rod has a diameter of 11 mm on entry into the former finger 12 and has a diameter of 6.8 mm at the exit, then at the place indicated in FIG. 1 there is a spacing between former band 10 and former finger 12 amounting to 7.85 mm, i.e. corresponding to the diameter of the tobacco rod of a finished cigarette. The packing density of the rod of tobacco fibres at this place also corresponds to the packing density of the finished rod of tobacco fibres and thus its hardness.

The return force of the tobacco rod against the compacting effect exerted by the former finger, thus the frictional forces between tobacco rod and former finger 12, and thus, finally, the temperature produced by these frictional forces, correlates very precisely with the return or restoring force of the finished smokable article, for example a cigarette, i.e. the temperature of the former finger represents an exact and reproducible measure of the hardness of the finished cigarette.

Figure 2:
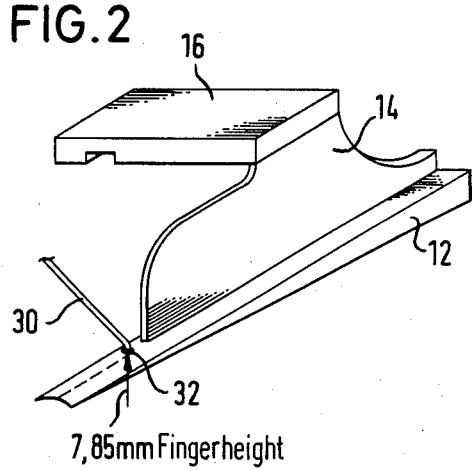
FIG. 2 shows a perspective view of a first form of embodiment of a device for continuous measurement of hardness.

In the form of embodiment shown in FIG. 2 a temperature pickup 30 is secured to the former finger 12, namely a thermocouple element, a semiconductor temperature sensor or a resistance thermometer. The temperature pickup 30 is arranged at the place 32 of the former finger at which the diameter of the tobacco rod corresponds to that of the finished cigarette.

Figure 3:
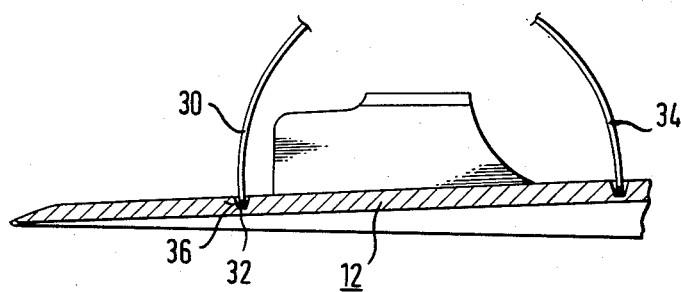
FIG. 3 shows a side view of a form of embodiment of a device for measuring the hardness, with two temperature pickups.

As FIG. 3 shows, the former finger 12 is provided at this region 32 with a blind hole which extends from the topside of the former finger 12 downwards to into the vicinity of its under-surface, the end wall remaining amounting to approximately 0.1 mm. The measuring element proper of the temperature pickup 30 is inserted into this blind hole.

Figure 4:
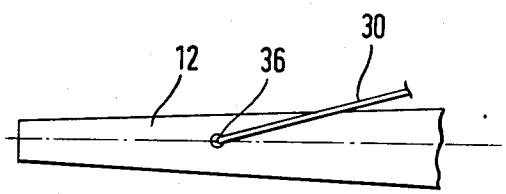
FIG. 4 shows a plan view on to the former finger with a temperature pickup inserted.

FIG. 4 shows a plan view on to this measuring arrangement i.e. a view of the topside of the former finger 12 with the temperature pickup 30 inserted in the bore 36.

FIG. 3 shows a variant wherein in addition to the temperature pickup 30 proper there is also provided a compensation temperature pickup 34 at the entry side of the former finger 12, and said additional pickup is also situated in a blind hole. A thermocouple element, a resistance thermometer or a semiconductor temperature sensor may also be used for this purpose.

Figure 5:
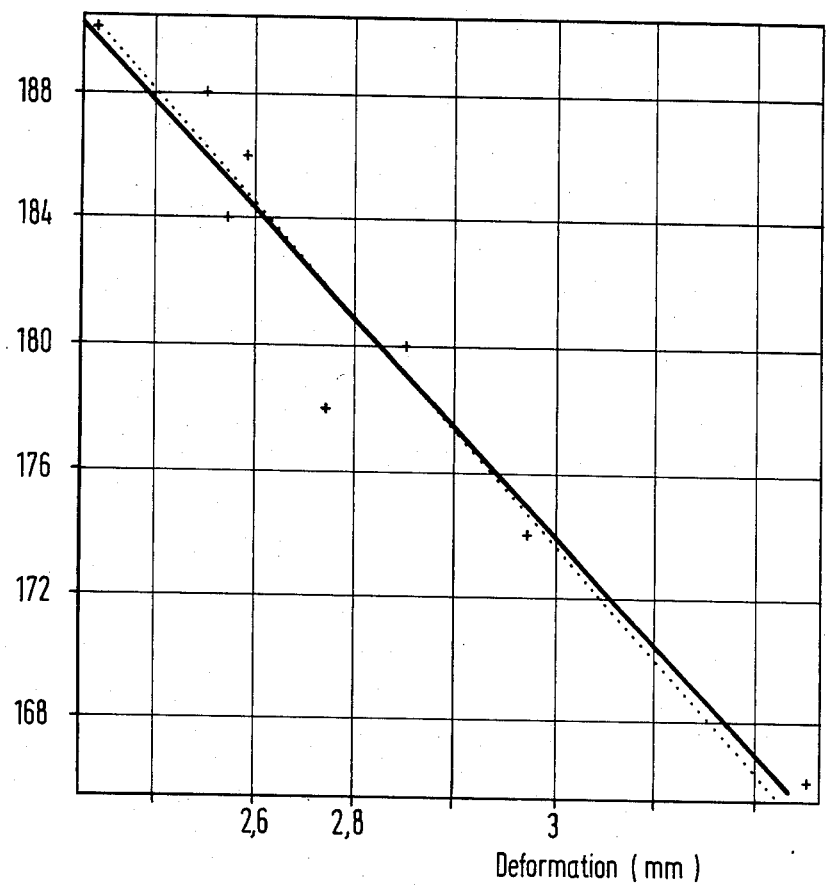
FIG. 5 shows a curve diagram wherein the temperature of the former finger in degrees C. is plotted over the corrected deformation of a finished cigarette, expressed in mm.

FIG. 5 shows a graph wherein the temperature in degrees C. ascertained in the region 32 by means of a single temperature pickup 30 is plotted over the deformation in mm, measured after a given time, of a cigarette under a predetermined load i.e. the hardness of the finished cigarette. It will be apparent that the temperature varies substantially linearly with the hardness. The correlation coefficient amounts to approximately b 99%.

It is also possible to read from the curve that when there is a change in deformation by 0.6 mm the temperature of the former finger changes by about 20° C., i.e. a sufficiently well-defined measurement signal is obtained which can easily be evaluated and used for adjusting production. For example it is possible to regulate the cigarette tobacco rod machine to continuous cigarette hardness, and both the position of the trimming discs and also the spreader speed can be considered as manipulated variables.

Automatic compensation for external influences, for example ambient temperature and the cooling effect of possible air currents, is achieved by use of the compensation temperature pickup 34.

If required, the electrical signal produced by one of these pickups can be linked with an electrical signal for moisture, such as is supplied for example by a moisture measuring device installed in the spreader of the tobacco rod machine; in this way a moisture-corrected cigarette hardness can be obtained. This is required since cigarette hardness fluctuates when there is varying tobacco moisture, other conditions being equal.

We claim:

1. In a device for the continuous determination of the hardness of a smokable article, during the manufacture of the smokable article with a former finger for compacting a rod of tobacco fibers to a given diameter, the improvement being that a temperature sensing device is positioned at a point on the former finger so as to ascertain the temperature of the former finger, by providing a measurement signal for monitoring the temperature of the former finger, said hardness determination being based upon correlation to the heat produced by frictional forces between the rod of tobacco fibers and the underside of the former finger.

2. Device according to claim 1, in which a resistance thermometer is used as temperature pickup.

3. Device according to claim 1, in which a thermocouple element is used as temperature pickup.

4. Device according to claim 1, in which a semiconductor temperature sensor is used as temperature pickup.

5. Device according to claim 1 in which the temperature pickup is situated at a region of the former finger at which the diameter of the rod of tobacco fibres corresponds approximately to the tobacco diameter of the finished smokable article.

6. Device according to claim 5, in which the temperature pickup is arranged in a blind hole which extends from the topside of the former finger in the direction towards the rod of tobacco fibres.

7. Device according to claim 6, in which the spacing between the end of the blind hole and the undersurface of the former finger is as small as possible.

8. Device according to claim 1, in which a second temperature pickup is arranged at the entry portion of the former finger, the computed value from the output signals of the two temperature pickups being used as the measurement signal.

9. Device according to claim 8, in which a resistance thermometer, thermocouple element or semiconductor temperature sensor is used as the second temperature pickup.

10. Device according to claim 8, in which the two temperature pickups are arranged in the middle of the former finger as viewed in the direction in which the rod of tobacco fibres is transported.

* * * * *